United States Patent
Gers-Barlag et al.

(10) Patent No.: US 6,180,090 B1
(45) Date of Patent: Jan. 30, 2001

(54) USE OF POLYSACCHARIDES FOR IMPROVING THE LIGHT PROTECTION EFFECT OF COSMETIC OR DERMATOLOGICAL LIGHT PROTECTION COMPOSITIONS

(75) Inventors: Heinrich Gers-Barlag, Kummerfeld; Rainer Kröpke, Schenefeld; Oliver Scheel, Düsseldorf; Jens Nielsen, Henstedt-Ulzburg, all of (DE)

(73) Assignee: Beiersdorf AG, Hamburg (DE)

( * ) Notice: Under 35 U.S.C. 154(b), the term of this patent shall be extended for 0 days.

(21) Appl. No.: 09/195,081

(22) Filed: Nov. 18, 1998

(30) Foreign Application Priority Data

Dec. 5, 1997 (DE) ............................................. 197 54 037

(51) Int. Cl.⁷ ................ A61K 7/42; A61K 7/44; A61K 7/00

(52) U.S. Cl. ................................ 424/59; 424/60; 424/400; 424/401

(58) Field of Search ................................ 424/59, 60, 400, 424/401

(56) References Cited

U.S. PATENT DOCUMENTS

| | | | |
|---|---|---|---|
| 5,169,624 | * | 12/1992 | Ziegler et al. .......................... 424/59 |
| 5,725,844 | * | 3/1998 | Gers-Barlag et al. .................. 424/59 |
| 5,728,372 | * | 3/1998 | Pinzon .................................... 424/59 |

* cited by examiner

*Primary Examiner*—Shelley A. Dodson
(74) *Attorney, Agent, or Firm*—Norris, McLaughlin & Marcus, P.A.

(57) ABSTRACT

Use of polysaccharides for increasing the light protection factor of cosmetic or dermatological preparations which comprise at least one customary UV filter substance.

10 Claims, No Drawings

USE OF POLYSACCHARIDES FOR IMPROVING THE LIGHT PROTECTION EFFECT OF COSMETIC OR DERMATOLOGICAL LIGHT PROTECTION COMPOSITIONS

The present invention relates to light protection formulations, in particular to cosmetic and dermatological light protection compositions.

The damaging effect of the ultraviolet part of solar radiation on the skin is generally known. While rays having a wavelength of below 290 nm (the UVC region) are absorbed by the ozone layer in the Earth's atmosphere, rays in the region between 290 nm and 320 nm, the UVB region, cause erythema, simple sunburn or even burns of varying severity.

The maximum erythema activity of sunlight is in the narrower region around 308 nm.

Numerous compounds for protecting against UVB radiation are known; these are usually derivatives of 3-benzylidenecamphor, 4-aminobenzoic acid, cinnamic acid, salicylic acid, benzophenone and also 2-phenylbenzimidazole.

It is also important to have available filter substances, for the region between about 320 nm and about 400 nm, the UVA region, since the rays of that region can also cause damage. For example, it has been found that UVA radiation leads to damage of the elastic and collagenic fibres of connective tissue, causing premature ageing of the skin, and it is regarded as a cause of numerous phototoxic and photoallergic reactions. The damaging effect of UVB radiation can be intensified by UVA radiation.

For protecting against the rays of the UVA region, use is therefore made of certain derivatives of dibenzoylmethane, whose photostability (Int. J. Cosm. Science 10, 53 (1988)) is inadequate.

However, UV radiation can also lead to photochemical reactions, in which case the photochemical reaction products intervene in the skin's metabolism. Such photochemical reaction products are predominantly free-radical compounds, for example hydroxyl free radicals. Undefined free-radical photoproducts which are formed in the skin itself can also display uncontrolled secondary reactions because of their high reactivity. However, singlet oxygen, a non-radical excited state of the oxygen molecule, can also be formed during UV irradiation, as can short-lived epoxides and many others. Singlet oxygen, for example, differs from normal triplet oxygen (free-radical ground state) by its increased reactivity. However, excited, reactive (free-radical) triplet states of the oxygen molecule also exist.

In order to prevent these reactions, it is possible additionally to incorporate antioxidants and/or free-radical scavengers into the cosmetic or dermatological formulations.

Known and advantageous light protection substances are dibenzoylmethane derivatives, for example 5-isopropyidibenzoylmethane (CAS No. 63250-25-9), which is characterized by the structure

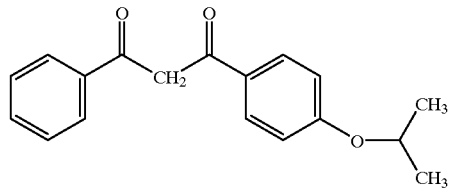

and is marketed by Merck under the name Eusolex® 8020, and also 4-(tert-butyl)-4'-methoxydibenzoylmethane (CAS No. 70356-09-1), which is characterized by the structure

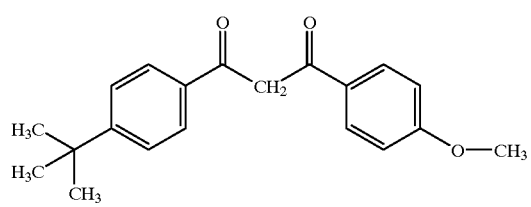

and marketed by Givaudan under the name Parsol® 1789. However, in combination with other substances present as solids, their use concentration is limited. There are therefore certain formulation difficulties in achieving higher light protection factors.

Another advantageous light protection filter substance is 4-methylbenzylidenecamphor, which is characterized by the structure

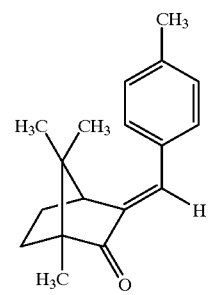

and is marketed by Merck under the name Eusolex® 6300. 4-Methylbenzylidenecamphor is an extremely advantageous light protection filter substance, which is a solid under normal conditions and is notable per se for good UV filter properties. In combination with other solid substances, however, its use concentration too is limited. There are thus certain formulation difficulties in achieving higher light protection factors here as well.

Other benzylidenecamphor derivatives are also advantageous light protection filter substances, e.g. benzylidenecamphor, which is characterized by the structure

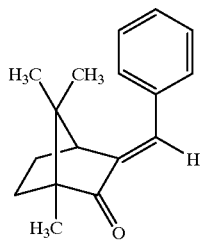

and is marketed by Induchem under the name Unisol® S22. In combination with other substances in the form of solids, however, its use concentration too is limited. There are thus certain formulation difficulties in achieving higher light protection factors here as well.

Another advantageous UV filter is tris(2-ethylhexyl) 4,4', 4"-(1,3,5-triazine-2,4,6-triyltriimino)trisbenzoate, synonym: 2,4,6-tris[anilino(p-carbo-2'-ethyl-1'-hexyloxy)]-1,3,5-triazine.

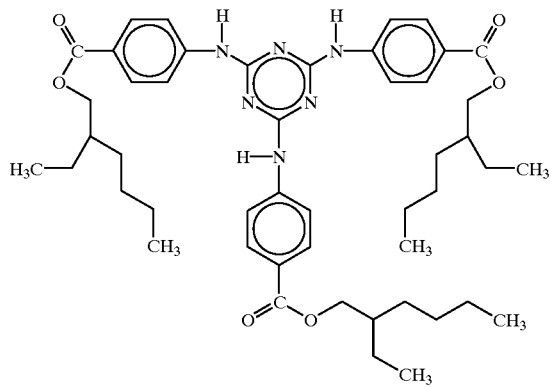

This UVB filter substance is marketed by BASF Aktiengesellschaft under the trade name UVINUL® T 150 and is notable for good UV absorption properties. In the meantime, various authors have described other UV filter substances which have the structure

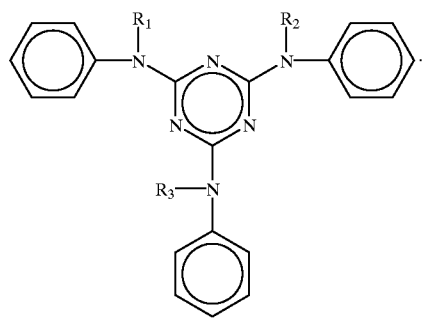

The main disadvantage of tris(2-ethylhexyl) 4,4', 4"-(1,3,5-triazine-2,4,6-triyltriimino)trisbenzoate is its poor solubility in lipids. Known solvents for this UVB filter can dissolve a maximum of about 15% by weight of this filter, corresponding to about 1–1.5% by weight of dissolved, and thus active, UV filter substance. There are thus certain formulation difficulties in achieving high light protection factors here as well.

Other UV filter substances which are in the form of solids, the incorporation of which into cosmetic or dermatological light protection formulations has at least certain problems, are also known. For example, EP-A-570 838 describes s-triazine derivatives, the chemical structure of which is given by the generic formula

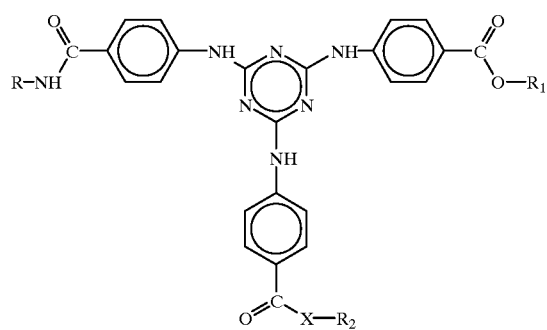

where

R is a branched or unbranched $C_1$–$C_{18}$-alkyl radical, a $C_5$–$C_{12}$-cycloalkyl radical, optionally substituted with one or more $C_1$–$C_4$-alkyl groups, X is an oxygen atom or an NH group, $R_1$ is a branched or unbranched $C_1$–$C_{18}$-alkyl radical, a $C_5$–$C_{12}$-cycloalkyl radical, optionally substituted with one or more $C_1$–$C_4$-alkyl groups, or a hydrogen atom, an alkali metal atom, an ammonium group or a group of the formula

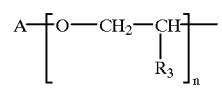

in which

A is a branched or unbranched $C_1$–$C_{18}$-alkyl radical, a $C_5$–$C_{12}$-cycloalkyl or aryl radical, optionally substituted with one or more $C_1$–$C_4$-alkyl groups, $R_3$ is a hydrogen atom or a methyl group, n is a number from 1 to 10, $R_2$ is a branched or unbranched $C_1$–$C_{18}$-alkyl radical, a $C_5$–$C_{12}$-cycloalkyl radical, optionally substituted with one or more $C_1$–$C_4$-alkyl groups, when X is the NH group, and a branched or unbranched $C_1$–$C_{18}$-alkyl radical, a $C_5$–$C_{12}$-cycloalkyl radical, optionally substituted with one or more $C_1$–$C_4$-alkyl groups, or a hydrogen atom, an alkali metal atom, an ammonium group or a group of the formula

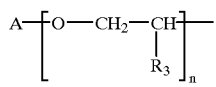

in which

A is a branched or unbranched $C_1$–$C_{18}$-alkyl radical, a $C_5$–$C_{12}$-cycloalkyl or aryl radical, optionally substituted with one or more $C_1$–$C_4$-alkyl groups, $R_3$ is a hydrogen atom or a methyl group, n is a number from 1 to 10, when X is an oxygen atom.

Even if it is in principle possible to achieve a certain UV protection for a given limited solubility (and thus, according to traditional standards, poor incorporability into a cosmetic or dermatological preparation), another problem may arise, that of recrystallization. In the case of sparingly soluble substances, this happens comparatively quickly, be it as a result of fluctuations in temperature or other influences. Uncontrolled recrystallization of an essential constituent of the preparation, such as a UV filter, does, however, have extremely disadvantageous effects on the properties of the given preparation and, not least, on the desired light protection.

Other UV filter substances, incorporation of which into cosmetic or dermatological light protection formulations has at least certain problems, are also known. For example, EP-A-775 698 describes bisresorcinyltriazine derivatives, the chemical structure of which is given by the generic formula

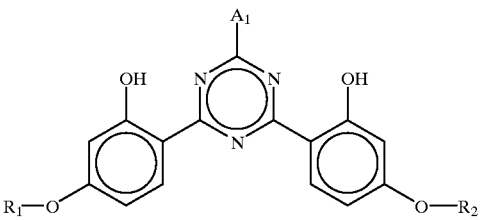

where $R_1$, $R_2$ and $A_1$ represent a wide variety of organic radicals.

Advantageous bisresorcinyltriazine derivatives are, for example, the following compounds:

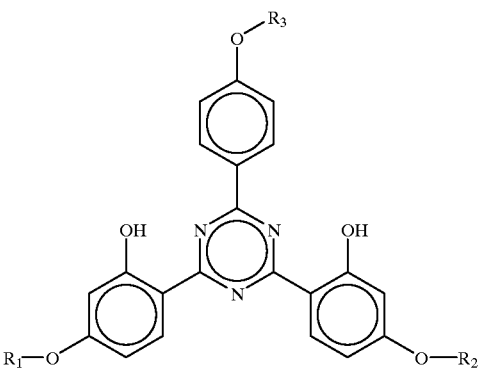

where $R_3$ is a hydrogen atom or a branched or unbranched alkyl group having from 1 to 10 carbon atoms, in particular 2,4-bis{[4-(2-ethylhexyloxy)-2-hydroxy]-phenyl }-6-(4-methoxyphenyl)-1,3,5-triazine, which is characterized by the following structure:

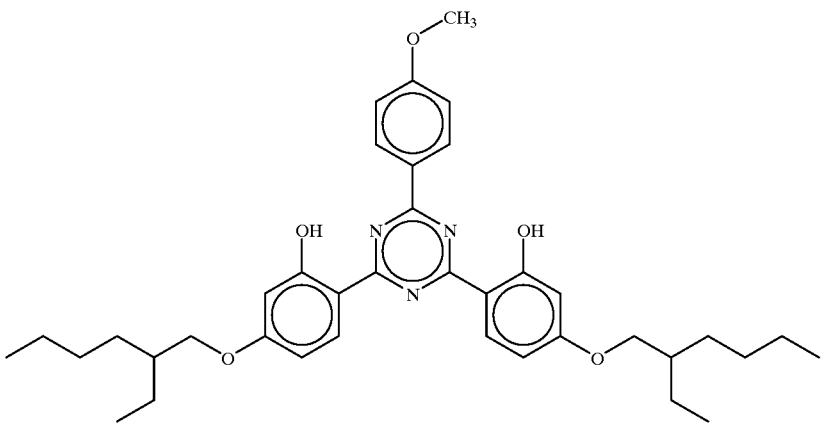

Another advantageous compound is 2,4-bis{[4-(3-sulphonato)-2-hydroxypropoxy)-2-hydroxy]phenyl}-6-(4-methoxyphenyl)-1,3,5-triazine, sodium salt, which is characterized by the following structure:

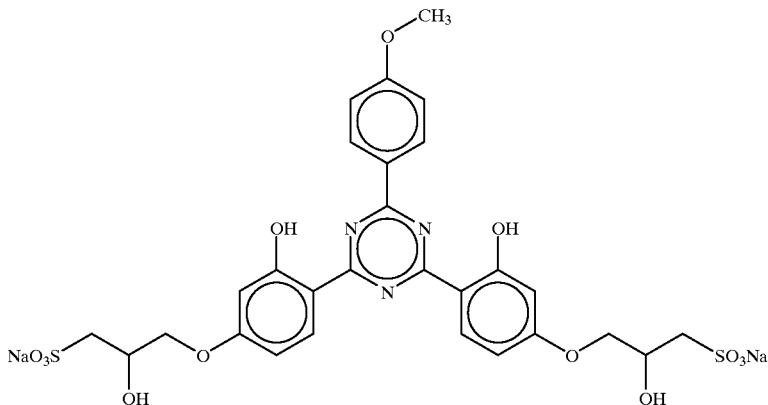

Another advantageous compound is 2,4-bis{[4-(3-(2-propoxy)-2-hydroxy-propoxy)-2-hydroxy]phenyl}-6-(4-methoxyphenyl)-1,3,5-triazine, which is characterized by the following structure:

Another advantageous compound is 2,4-bis{[4-(3-(2-propoxy)-2-hydroxy-propoxy)-2-hydroxy]phenyl}-6-[4-(2-ethylcarboxyl)phenylamino]-1,3,5-triazine, which is characterized by the following structure:

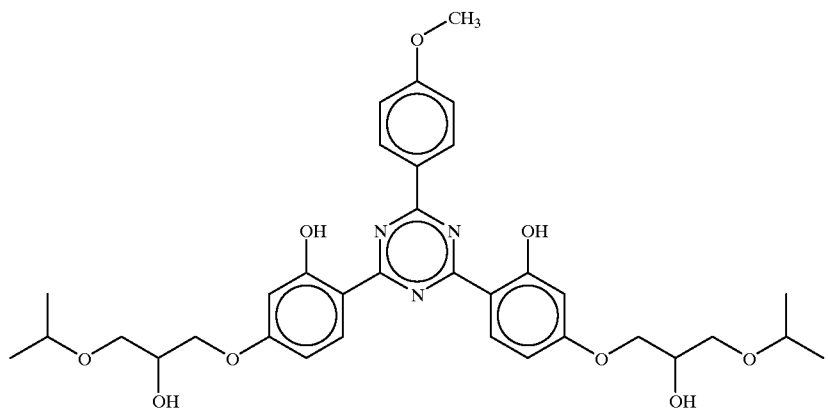

Another advantageous compound is 2,4-bis{[4-(2-ethylhexyloxy)-2-hydroxy]-phenyl}-6-[4-(2-methoxyethylcarboxyl)phenylamino]-1,3,5-triazine, which is characterized by the following structure:

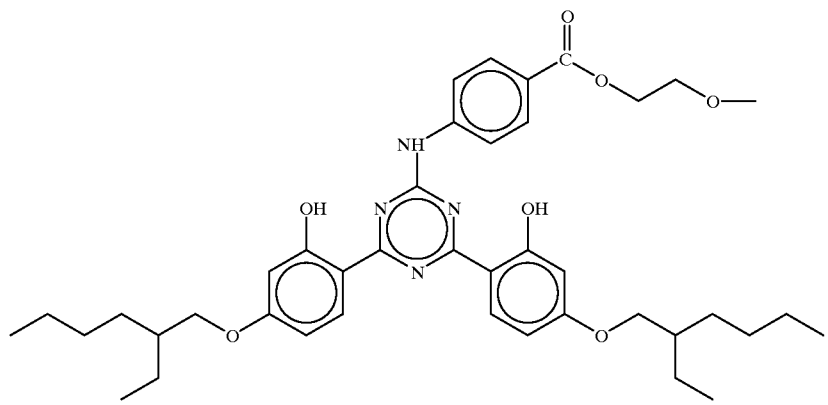

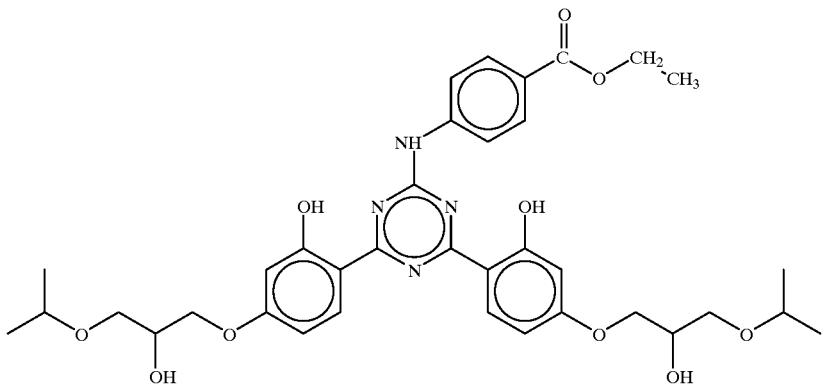

Another advantageous compound is 2,4-bis{[4-(2-ethylhexyloxy)-2-hydroxy]-phenyl}-6-(1-methylpyrrol-2-yl)-1,3,5-triazine, which is characterized by the following structure:

Another advantageous compound is 2,4-bis{[4-(2"-methylpropenyloxy)-2-hydroxy]phenyl}-6-(4-methoxyphenyl)-1,3,5-triazine, which is characterized by the following structure:

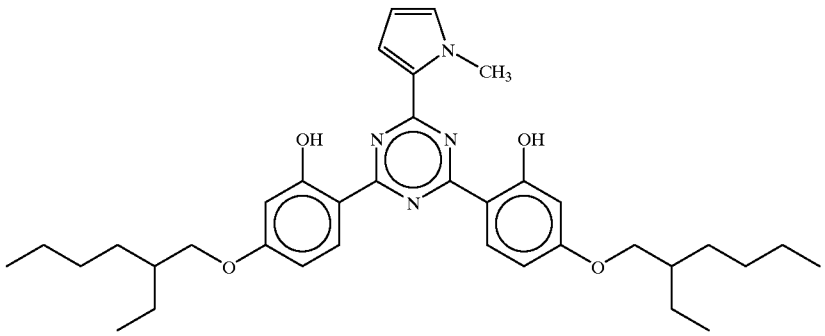

Another advantageous compound is 2,4-bis{[4-tris(trimethylsiloxysilylpropoxy)-2-hydroxy]phenyl}-6-(4-methoxyphenyl)-1,3,5-triazine, which is characterized by the following structure:

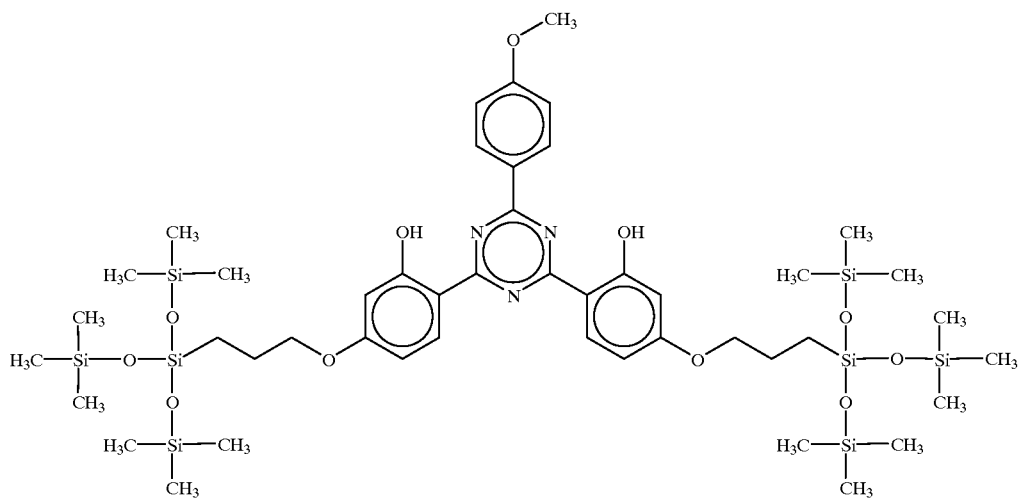

Another advantageous compound is 2,4-bis{[4-(1',1', 1',3',5',5',5'-heptamethyl-siloxy-2"-methylpropoxy)-2-hydroxy]phenyl}-6-(4-methoxyphenyl)-1,3,5-triazine, which is characterized by the following structure:

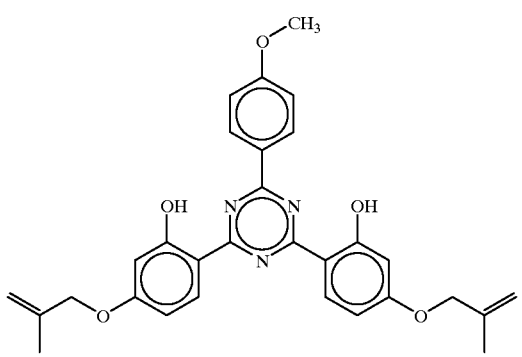

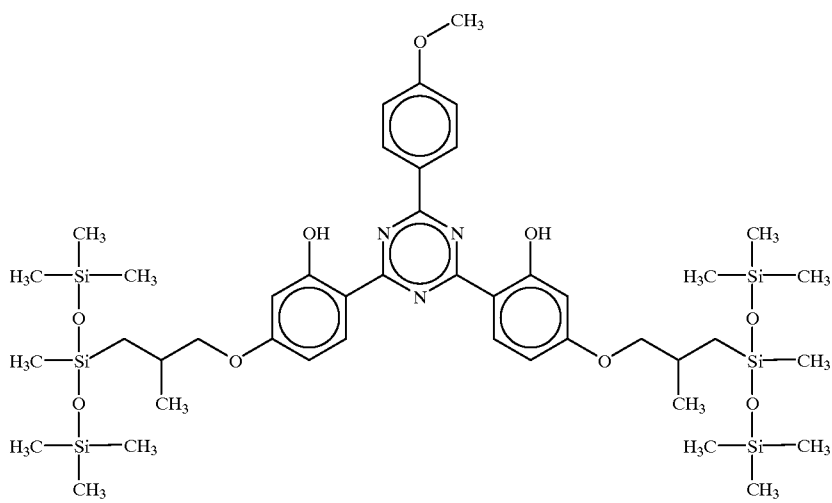

Even if it is in principle possible to achieve a certain UV protection for a given limited solubility (and thus, according to traditional standards, poor incorporability into a cosmetic or dermatological preparation) with bisresorcinyltriazine derivatives, another problem may arise, that of recrystallization. In the case of sparingly soluble substances, this happens comparatively quickly, be it as a result of fluctuations in temperature or other influences. Uncontrolled recrystallization of an essential constituent of the preparation, such as UV filter, does, however, have extremely disadvantageous effects on the properties of the given preparation and, not least, on the desired light protection.

Another advantageous UV filter is 2,2'-methylenebis(6-(2H-benzotriazol-2-yl)-4-(1,1,3,3-tetramethylbutyl)phenol), which is characterized by the chemical structural formula

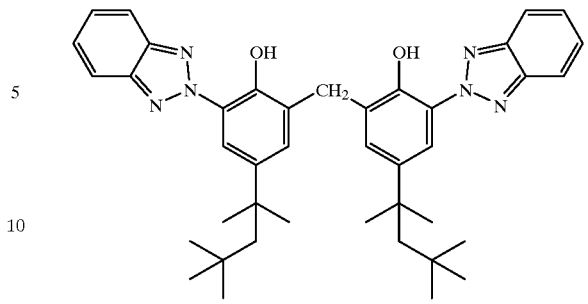

In the case of this substance too, there are, however, certain formulation disadvantages when large amounts are used since this substance is sparingly soluble. Using this substance, it is therefore difficult to achieve high light protection factors.

The compounds which are used as light protection agents for cosmetic and dermatological light protection formulations, some of which are given above, are notable per se, as already stated, for good light protection effects.

However, they have the disadvantage that it is at times difficult to incorporate them into such formulations in a satisfactory manner.

Generally speaking, the light absorption behaviour of light protection filter substances is very well known and documented, not least because most industrialized countries have a positive list for the use of such substances, which imposes relatively strict standards on the documentation. For the concentration of the substances in the finished formulations, the absorbance values can at best be a guide, since interactions with substances within the skin or within the surface of the skin itself may result in imponderabilities. In addition, it is usually difficult to estimate in advance how uniformly and in what layer thickness the filter substance is distributed in and on the horny layer of the skin.

The light protection factor (LPF, often also known as SPF for sun protection factor) indicates how much longer the skin protected with the light protection agent can be exposed until the same erythemal reaction takes place as would occur in the case of unprotected skin (i.e. ten times longer compared with unprotected skin for LPF=10).

In any case, the consumer expects, on the one hand, reliable information from the manufacturer regarding the light protection factor—not least because of the discussion about the "hole in the ozone layer" which has become a topic of public interest, and on the other hand there is a tendency by the consumer towards higher and high light protection factors.

Since light protection filter substances are usually costly, and since most light protection filter substances are also difficult to incorporate into cosmetic or dermatological preparations in relatively high concentrations, the object of the invention was to obtain, in a simple and low-cost manner, preparations which, in unusually low concentrations of conventional light protection filter substances, nevertheless achieve acceptable or even high LPF values.

It was therefore surprising and could not have been foreseen by the person skilled in the art that the use of polysaccharides for improving the light protection effect, in particular for increasing the light protection factor, of cosmetic or dermatological preparations which comprise at least one customary UV filter substance, would remedy the disadvantages of the prior art.

It is advantageous to use polysaccharides which are soluble in water and/or swellable in water and/or gellable with the help of water. It is particularly advantageous to use hyaluronic acid, chitosan and also other polysaccharides which are soluble in water and/or swellable in water and/or gellable with the help of water, for example a fucose-rich product, a polysaccharide listed in the Chemical Abstracts under the registry number 178463-23-5, which is obtainable under the name Fucogel® 1000 from SOLABIA S.A. The latter is characterized by structural elements as follows:

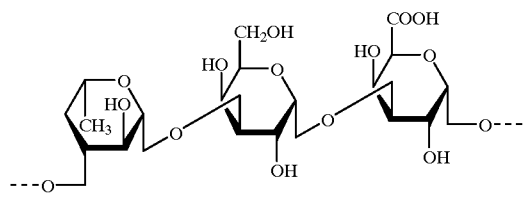

Hyaluronic acid is characterized by the structure

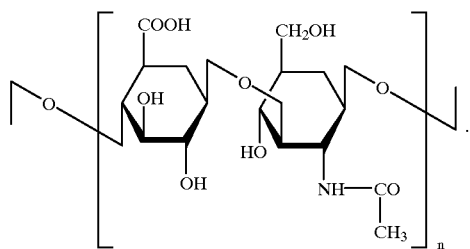

When hyaluronic acid is the or one of the polysaccharides used, it is advantageous to choose one with molecular weights between 30,000 and 8,000,000, in particular one with molecular weights between 500,000 and 1,500,000.

Chitosan is characterized by the following structural formula:

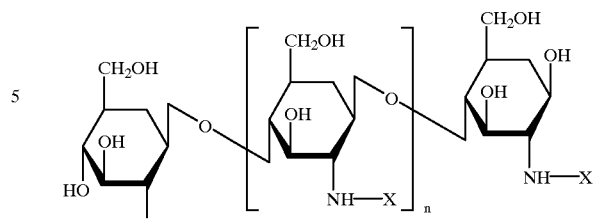

where n is a value up to about 2,000, and X is either the acetyl radical or hydrogen. Chitosan is formed by deacetylation and partial depolymerization (hydrolysis) of chitin, which is characterized by the structural formula

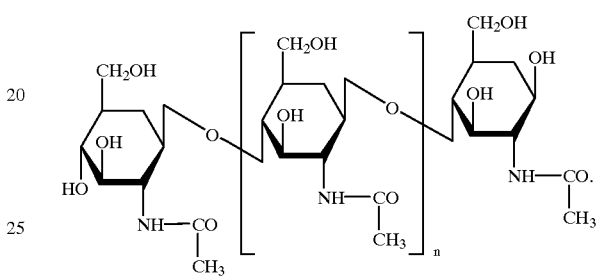

Chitin is an essential constituent of the exoskeleton ['o citwn=Greek for integument] of arthropods (e.g. insects, crabs, spiders) and is also found in supporting tissue of other organisms (e.g. molluscs, algae, fungi).

Chitosan is a raw material known in hair care. It is suitable, to a higher degree than the chitin on which it is based, as a thickener or stabilizer and improves the adhesion and water resistance of polymeric films. A representative of a large number of literature references for the prior art is: H. P. Fiedler, "Lexikon der Hilfsstoffe für Pharmazie, Kosmetik und angrenzende Gebiete" [Lexicon of auxiliaries for pharmacy, cosmetics and related fields], third edition 1989, Editio Cantor, Aulendorf, p. 293, key word "chitosan".

According to the invention, preference is given to chitosans having a degree of deacetylation of >60%, in particular >80%. Of these, particular preference is given to those whose 1% strength aqueous solution has a viscosity of 4,500–5,500 mPas (Brookfield, spindle 5, 10 rpm), in particular 5,000 mPas.

If chitosan is the or one of the polysaccharides used, it is advantageous to choose one with molecular weights between 3,000 and 2,000,000, in particular one with molecular weights between 10,000 and 500,000.

According to the invention, cosmetic or dermatological light protection preparations comprise from 0.1 to 20% by weight, advantageously from 0.5 to 10% by weight, very particularly preferably from 1 to 5% by weight, of polysaccharides.

It was surprising that the polysaccharides within the meaning of the present invention result in an increase in the light protection factor since these pigments themselves have no pronounced absorption in the UVA or UVB region.

In particular, it was surprising that the polysaccharides within the meaning of the present invention result in an increase in the light protection factor when at least one of the UV filters in the light protection preparations according to the present invention is chosen from the group of triazine derivatives, in particular chosen from the group tris(2-ethylhexyl) 4,4',4"-(1,3,5-triazine-2,4,6-triyltriimino)trisbenzoate 2,4-bis{[4-(2-ethylhexyloxy)-2-hydroxy]phenyl}-6-(4-methoxyphenyl)-1,3,5-triazine, 2,4-bis{[4-(3-sulphonato)-2-hydroxypropoxy)-2-hydroxy]phenyl}-6-(4-methoxyphenyl)-1,3,5-triazine, sodium salt, 2,4-bis{[4-(3-(2-propoxy)-2-hydroxypropoxy)-2-hydroxy]phenyl}-6-(4-methoxyphenyl)-1,3,5-triazine, 2,4-bis-{[4-(2-ethylhexyloxy)-2-hydroxy]phenyl}-6-[4-(2-methoxyethyl-carboxyl)phenylamino]-1 ,3,5-triazine, 2,4-bis{[4-(3-(2-propoxy)-2-hydroxypropoxy)-2-hydroxy]phenyl}-6-[4-(2-ethylcarboxyl)phenylamino]-1,3,5-triazine, 2,4-bis{[4-(2-ethylhexyloxy)-2-hydroxy]phenyl }-6-(1-methylpyrrol-2-yl)-1,3,5-triazine, 2,4-bis{[4-tris(trimethylsiloxysilylpropoxy)-2-hydroxy]phenyl}-6-(4-methoxy-phenyl)-1,3,5-triazine, 2,4-bis{[4-(2"-methylpropenyloxy)-2-hydroxy]phenyl}-6-(4-methoxyphenyl)-1,3,5-triazine and 2,4-bis{[4-(1',1',1',3',5',5', 5'-heptamethylsiloxy-2"-methylpropoxy)-2-hydroxy]phenyl}-6-(4-methoxyphenyl)-1,3,5-triazine.

It was further surprising that the polysaccharides within the meaning of the present invention result in an increase in the light protection factor if at least one of the UV filters in the light protection preparations according to the present invention is 2,2'-methylenebis(6-(2H-benzotriazol-2-yl)-4-(1,1,3,3-tetramethylbutyl)phenol).

It is of particular advantage and characterized by independent inventive activity to keep the content of the novel preparations of polyols, in particular propylene glycol, butylene glycol, glycerol, but also polyoxyethylene and polyoxybutylene (PEGs) low. Thus, preparations according to the invention advantageously comprise a maximum of 3% by weight of polyols, preferably 2% by weight, particularly preferably 1% by weight and are very particularly preferably free of polyols.

Cosmetic and dermatological preparations according to the invention advantageously comprise, although it is not obligatory, inorganic pigments, which may be X-ray amorphous and/or not, based on metal oxides and/or other metal compounds which are insoluble or sparingly soluble in water, in particular the oxides of titanium ($TiO_2$), zinc (ZnO), iron (for example $Fe_2O_3$), zirconium ($ZrO_2$), silicon ($SiO_2$), manganese (for example MnO), aluminium ($Al_2O_3$) or cerium (for example $Ce_2O_3$), mixed oxides of the corresponding metals and mixtures of such oxides. The pigments are particularly preferably those based on $TiO_2$.

According to the invention, it is advantageous if the inorganic pigments are present in hydrophobic form, i.e. if they have been surface-treated to repel water. This surface treatment may involve providing the pigments with a thin hydrophobic layer by processes known per se.

Such a process involves, for example, producing the hydrophobic surface layer by a reaction according to

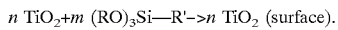

n and m here are stoichiometric parameters to be employed as desired, and R and R'are the desired organic radicals. Hydrophobicized pigments prepared analogously to DE-A 33 14 742, for example, are advantageous.

Advantageous $TiO_2$ pigments are obtainable, for example, under the trade names T 805 from Degussa.

X-ray amorphous oxide pigments are metal oxides or semimetal oxides which reveal no or no recognizable crystal structure in X-ray diffraction experiments. Such pigments are often obtainable by flame reaction, for example by reacting a metal or semimetal halide with hydrogen and air (or pure oxygen) in a flame.

Known X-ray amorphous oxide pigments which are often used in cosmetic or dermatological galenics are the silixon oxides of the Aerosil® type (CAS No. 7631-86-9. Aerosils®, obtainable from DEGUSSA, are characterized by small particle size (e.g. between 5 and 40 nm), the particles being regarded as spherical particles of very uniform dimension. Macroscopically, Aerosils® are recognizable as loose white powders. For the purposes of the present invention, X-ray amorphous silicon dioxide pigments are particularly advantageous, and, of these, those of the Aerosil® type are preferred.

Advantageous Aerosil® products are, for example, Aerosil® OX50, Aerosil® 130, Aerosil® 150, Aerosil® 200, Aerosil® 300, Aerosil® 380, Aerosil® MOX 80, Aerosil® MOX 170, Aerosil® COK 84, Aerosil® R 202, Aerosil® R 805, Aerosil® R 812, Aerosil® R 972, Aerosil® R 974, Aerosil® R976.

According to the invention, cosmetic or dermatological light protection preparations comprise from 0.1 to 20% by weight, advantageously from 0.5 to 10% by weight, very particularly preferably from 1 to 5% by weight, of X-ray-amorphous oxide pigments.

The total amount of inorganic pigments, in particular hydrophobic inorganic micropigments, in the finished cosmetic or dermatological preparations is advantageously chosen from the range 0.1–30% by weight, preferably 0.1–10.0% by weight, in particular 0.5–6.0% by weight, based on the total weight of the preparations.

The cosmetic and/or dermatological light protection formulations according to the invention can have the customary composition and can be used for cosmetic and/or dermatological light protection, and furthermore for the treatment, care and cleansing of the skin and/or hair and as a make-up product in decorative cosmetics.

For use, the cosmetic and dermatological preparations according to the invention are applied to the skin and/or hair in an adequate amount in the manner customary for cosmetics.

Particularly preferred cosmetic and dermatological preparations are those which are in the form of a sunscreen composition. These can advantageously additionally comprise at least one further UVA filter and/or at least one further UVB filter and/or at least one inorganic pigment, preferably an inorganic micropigment.

The cosmetic and dermatological preparations according to the invention can comprise cosmetic auxiliaries such as are usually used in such preparations, for example preservatives, bactericides, perfumes, antifoams, dyes, pigments which have a colouring action, thickeners, moisturizers and/or humectants, fats, oils, waxes or other customary constituents of a cosmetic or dermatological formulation, such as alcohols, polyols, polymers, foam stabilizers, electrolytes, organic solvents or silicone derivatives.

An additional content of antioxidants is generally preferred. According to the invention, favourable antioxidants which can be used are all the antioxidants which are suitable or customary for cosmetic and/or dermatological uses.

The antioxidants are advantageously chosen from the group consisting of amino acids (for example glycine, histidine, tyrosine, tryptophan) and derivatives thereof, imidazoles (for example urocanic acid) and derivatives thereof, peptides such as D,L-carnosine, D-carnosine, L-carnosine and derivatives thereof (for example anserine), carotenoids, carotenes (for example α-carotene, β-carotene, lycopene) and derivatives thereof, chlorogenic acid and derivatives thereof, lipoic acid and derivatives thereof (for example dihydrolipoic acid), aurothioglucose, propylthiouracil and other thiols (for example thioredoxin, glutathione, cysteine, cystine, cystamine and the glycosyl, N-acetyl, methyl, ethyl, propyl, amyl, butyl and lauryl, paimitoyl, oleyl, γ-linoleyl, cholesteryl and glyceryl esters thereof) and salts thereof, dilauryl thiodipropionate, distearyl thiodipropionate, thiodipropionic acid and derivatives thereof (esters, ethers, peptides, lipids, nucleotides, nucleosides and salts) and sulphoximine compounds (for example buthionine-sulphoximines, homocysteine-sulphoximine, buthionine-sulphones, penta-, hexa- and hepta-thionine-sulphoximine) in very low tolerated doses (for example pmol to $\mu$mol/kg), and furthermore (metal) chelating agents (for example α-hydroxy-fatty acids, palmitic acid, phytic acid, lactoferrin), α-hydroxy acids (for example citric acid, lactic acid, malic acid), humic acid, bile acid, bile extracts, bilirubin, biliverdin, EDTA, EGTA and derivatives thereof, unsaturated fatty acids and derivatives thereof (for example γ-linolenic acid, linoleic acid, ofeic acid), folic acid and derivatives thereof, ubiquinone and ubiquinol and derivatives thereof, vitamin C and derivatives (for example ascorbyl palmitate, Mg ascorbyl phosphate, ascorbyl acetate), tocopherols and derivatives (for example vitamin E acetate), vitamin A and derivatives (vitamin A palmitate) and coniferyl benzoate of benzoin resin, rutic acid and derivatives thereof, α-glycosylrutin, ferulic acid, furfurylideneglucitol, carnosine, butylated hydroxytoluene, butylated hydroxyanisole, nordihydroguaiac resin acid, nor-dihydroguaiaretic acid, trihydroxybutyrophenone, uric acid and derivatives thereof, mannose and derivatives thereof, zinc and derivatives thereof (for example ZnO, $ZnSO_4$), selenium and derivatives thereof (for example selenium methionine), stilbenes and derivatives thereof (for example stilbene oxide, trans-stilbene oxide) and the derivatives of these active ingredients mentioned which are suitable according to the invention (salts, esters, ethers, sugars, nucleotides, nucleosides, peptides and lipids).

The amount of the abovementioned antioxidants (one or more compounds) in the preparations is preferably from 0.001 to 30% by weight, particularly preferably 0.05–20% by weight, in particular 1–10% by weight, based on the total weight of the preparation.

If vitamin E and/or derivatives thereof is or are the antioxidant or antioxidants, it is advantageous to choose the respective concentrations thereof from the range 0.001–10% by weight, based on the total weight of the formulation.

If vitamin A or vitamin A derivatives or carotenes or derivatives thereof is or are the antioxidant or antioxidants, it is advantageous to choose the respective concentrations thereof from the range 0.001–10% by weight, based on the total weight of the formulation.

The lipid phase can advantageously be chosen from the following group of substances:

mineral oils, mineral waxes oils, such as triglycerides of capric or of caprylic acid, and also natural oils such as castor oil;

fats, waxes and other natural and synthetic fatty substances, preferably esters of fatty acids with alcohols of low C number, for example with isopropanol, propylene glycol or glycerol, or esters of fatty alcohols with alkanoic acids of low C number or with fatty acids;

alkyl benzoates;

silicone oils, such as dimethylpolysiloxanes, diethylpolysiloxanes, diphenylpolysiloxanes and mixed forms thereof.

The oil phase of the emulsions, oleogels or hydrodispersions or lipodispersions for the purposes of the present invention is advantageously chosen from the group of esters of saturated and/or unsaturated, branched and/or unbranched alkanecarboxylic acids having a chain length of from 3 to 30 carbon atoms and saturated and/or unsaturated, branched and/or unbranched alcohols having a chain length of from 3 to 30 carbon atoms, from the group of esters of aromatic carboxylic acids and saturated and/or unsaturated, branched and/or unbranched alcohols having a chain length of from 3 to 30 carbon atoms. Such ester oils can in turn advantageously be chosen from the group consisting of isopropyl myristate, isopropyl palmitate, isopropyl stearate, isopropyl oleate, n-butyl stearate, n-hexyl laurate, n-decyl oleate, isooctyl stearate, isononyl stearate, isononyl isononanoate, 2-ethylhexyl palmitate, 2-ethylhexyl laurate, 2-hexyldecyl stearate, 2-octyldodecyl palmitate, oleyl oleate, oleyl erucate, erucyl oleate, erucyl erucate and also synthetic, semisynthetic and natural mixtures of such esters, e.g. jojoba oil.

In addition, the oil phase can advantageously be chosen from the group of branched and unbranched hydrocarbons and hydrocarbon waxes, silicone oils, dialkyl ethers, the group of saturated or unsaturated, branched or unbranched alcohols, and also fatty acid triglycerides, specifically the triglyceryl ester of saturated and/or unsaturated, branched and/or unbranched alkanecarboxylic acids having a chain length of from 8 to 24, in particular 12–18 carbon atoms. The fatty acid triglycerides can, for example, be advantageously chosen from the group of synthetic, semisynthetic and natural oils, e.g. olive oil, sunflower oil, soya oil, peanut oil, rapeseed oil, almond oil, palm oil, coconut oil, palm kernel oil and more of the same type.

Any desired mixtures of such oil and wax components are also advantageous for the purposes of the present invention. It may also be advantageous in some circumstances to use waxes, for example cetyl palmitate, as the sole lipid component of the oil phase.

The oil phase is advantageously chosen from the group consisting of 2-ethylhexyl isostearate, octyldodecanol, isotridecyl isononanoate, isoeicosane, 2-ethylhexyl cocoate, $C_{12-15}$-alkyl benzoate, caprylic-capric acid triglyceride and dicaprylyl ether.

Particularly advantageous mixtures are those of $C_{12-15}$-alkylbenzoate and 2-ethylhexyl isostearate, mixtures of $C_{12-15}$-alkylbenzoate and isotridecyl isononanoate and also mixtures of $C_{12-15}$-alkylbenzoate, 2-ethylhexyl isostearate and isotridecyl isononanoate.

Of the hydrocarbons, paraffin oil, squalane and squalene are advantageous for the purposes of the present invention.

The oil phase may also advantageously have a content of cyclic or linear silicone oil or consist entirely of such oils, preference however being given to using, as well as the silicone oil or the silicone oils, an additional content of other oil phase components.

Cyclomethicone (octamethylcyclotetrasiloxane) is advantageously employed as the silicone oil to be used according to the invention. However, other silicone oils are also advantageous for the purposes of the present invention, for example hexamethylcyclotrisiloxane, polydimethylsiloxane and poly(methylphenylsiloxane).

Other particularly advantageous mixtures comprise cyclomethicone and isotridecyl isononanoate, and cyclomethicone and 2-ethylhexyl isostearate.

If appropriate, the aqueous phase of the preparations according to the invention advantageously comprises alcohols, diols or polyols of low C number and ethers thereof, preferably ethanol, isopropanol, propylene glycol, glycerol, ethylene glycol, ethylene glycol monoethyl or monobutyl ether, propylene glycol monomethyl, monoethyl or monobutyl ether, diethylene glycol monomethyl or monoethyl ether and analogous products, furthermore alcohols of low C number, for example ethanol, isopropanol, 1,2-propanediol and glycerol, and, in particular, one or more thickeners, which can advantageously be chosen from the group consisting of silicon dioxide, aluminium silicates, polysaccharides and derivatives thereof, for example hyaluronic acid, xanthan gum and hydroxypropylmethylcellulose, particularly advantageously from the group consisting of polyacrylates, preferably a polyacrylate from the Carbopol group, for example Carbopols of types 980, 981, 1382, 2984 and 5984, in each case individually or in combination.

According to the invention, the LPF is significantly increased by the use of polysaccharides in cosmetic or dermatological preparations comprising customary UVA filters and/or UVB filters in the lipid phase and/or in the aqueous phase.

In particular, the LPF is significantly increased by the use of polysaccharides in cosmetic or dermatological preparations comprising substances which absorb UV radiation in the UVB region, the total amount of such filter substances being, for example, from 0.1% by weight to 30% by weight, preferably from 0.5 to 20% by weight, in particular from 3 to 15% by weight, based on the total weight of the preparations.

Such UVB filters can be oil-soluble or water-soluble. Advantageous oil-soluble UVB filter substances are, for example:

3-benzylidenecamphor derivatives, preferably 3-(4-methylbenzylidene)camphor and 3-benzylidenecamphor;

4-aminobenzoic acid derivatives, preferably 2-ethylhexyl 4-(dimethylamino)benzoate and amyl 4-(dimethylamino)benzoate;

2,4,6-trianilino(p-carbo-2'-ethyl-1'-hexyloxy)-1,3,5-triazine;

esters of benzalmalonic acid, preferably di(2-ethylhexyl) 4-methoxybenzalmalonate;

esters of cinnamic acid, preferably 2-ethylhexyl 4-methoxycinnamate and isopentyl 4-methoxycinnamate;

derivatives of benzophenone, preferably 2-hydroxy-4-methoxybenzophenone, 2-hydroxy-4-methoxy-4'-methylbenzophenone and 2,2'-dihydroxy-4-methoxybenzophenone.

Advantageous water-soluble UVB filter substances are, for example:

salts of 2-phenylbenzimidazole-5-sulphonic acid, such as its sodium, potassium or its triethanol-ammonium salt, and the sulphonic acid itself;

sulphonic acid derivatives of 3-benzylidenecamphor, such as, for example, 4-(2-oxo-3-bornylidenemethyl) benzenesulphonic acid, 2-methyl-5-(2-oxo-3-bornylidenemethyl)benzenesulphonic acid and salts thereof.

The list of UVB filters mentioned which can additionally be used for the purposes of the present invention is not of course intended to be limiting.

In particular, the LPF is significantly increased by the use of polysaccharides in cosmetic or dermatological preparations comprising substances which absorb UV radiation in the UVA region, the total amount of such filter substances being, for example, from 0.1% by weight to 30% by weight, preferably from 0.5 to 10% by weight, in particular from 1 to 6% by weight, based on the total weight of the preparations.

It can also be very advantageous to use polymer-bound or polymeric UV filter substances in preparations in accordance with the present invention, in particular those described in WO-A-92/20690.

In particular, the LPF is significantly increased by the use of polysaccharides in cosmetic or dermatological preparations comprising polymer-bound or polymeric UV filter substances, the total amount of such filter substances being, for example, from 0.1% by weight to 30% by weight, preferably from 0.5 to 20% by weight, in particular from 3 to 15% by weight, based on the total weight of the preparations.

The total amount of water-soluble UV filter substances in the finished cosmetic or dermatological preparations is advantageously chosen from the range of 0.1–10.0% by weight, preferably 0.5–6.0% by weight, based on the total weight of the preparations.

The total amount of 2-phenylbenzimidazole-5-sulphonic acid or its salts in the finished cosmetic or dermatological preparations is, in cases where the presence of this substance is desired, advantageously chosen from the range 0.1–10.0% by weight, preferably 0.5–6.0% by weight, based on the total weight of the preparations.

The total amount of 2-hydroxy-4-methoxybenzophenone-5-sulphonic acid or its salts in the finished cosmetic or dermatological preparations is, in cases where the presence of this substance is desired, advantageously chosen from the range 0.1–10.0% by weight, preferably 0.5–6.0% by weight, based on the total weight of the preparations.

The total amount of 4-(2-oxo-3-bornylidenemethyl) benzenesulphonic acid or its salts in the finished cosmetic or dermatological preparations is, in cases where the presence of this substance is desired, advantageously chosen from the range 0.1–10.0% by weight, preferably 0.5–6.0% by weight, based on the total weight of the preparations.

The total amount of 2-methyl-5-(2-oxo-3-bornylidenemethyl)benzenesulphonic acid or salts thereof in the finished cosmetic or dermatological preparations is, in cases where the presence of this substance is desired, advantageously chosen from the range 0.1–10.0% by weight, preferably 0.5–6.0% by weight, based on the total weight of the preparations.

The total amount of benzene-1,4-di(2-oxo-3-bornylidenemethyl)-10-sulphonic acid or salts thereof in the finished cosmetic or dermatological preparations is, in cases where the presence of this substance is desired, advantageously chosen from the range 0.1–10.0% by weight, preferably 0.5–6.0% by weight, based on the total weight of the preparations.

The total amount of tris(2-ethylhexyl) 4,4',4''-(1,3,5-triazine-2,4,6-triyltriimino)tris-benzoate in the finished cosmetic or dermatological preparations is, in cases where the presence of this substance is desired, advantageously chosen from the range 0.1–10.0% by weight, preferably 0.5–6.0% by weight, based on the total weight of the preparations.

The total amount of 4-(tert-butyl)-4'-methoxydibenzoylmethane in the finished cosmetic or dermatological preparations is, in cases where the presence of this substance is desired, advantageously chosen from the range 0.1–10.0% by weight, preferably 0.5–6.0% by weight, based on the total weight of the preparations.

The total amount of 4-methylbenzylidenecamphor in the finished cosmetic or dermatological preparations is, in cases where the presence of this substance is desired, advantageously chosen from the range 0.1–10.0% by weight, preferably 0.5–6.0% by weight, based on the total weight of the preparations.

The total amount of 2-ethylhexyl-p-methoxycinnamate in the finished cosmetic or dermatological preparations is, in cases where the presence of this substance is desired, advantageously chosen from the range 0.1–15.0% by weight, preferably 0.5–7.5% by weight, based on the total weight of the preparations.

Another additional light protection filter substance which can be used advantageously according to the invention is ethylhexyl 2-cyano-3,3-diphenylacrylate (octocrylene), which is available from BASF under the name UVINUL® N 539 and is characterized by the following structure:

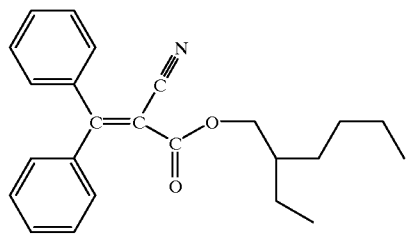

The total amount of ethylhexyl 2-cyano-3,3-diphenylacrylate in the finished cosmetic or dermatological preparations is, in cases where the presence of this substance is desired, advantageously chosen from range 0.1–15.0% by weight, preferably 0.5–10.0% by weight, based on the total weight of the preparations.

According to the invention, it may also in some circumstances be advantageous to incorporate other UVA and/or UVB filters into cosmetic or dermatological preparations, for example certain salicylic acid derivatives, such as 4-isopropylbenzyl salicylate, 2-ethylhexyl salicylate (=octyl salicylate), and homomenthyl salicylate.

The total amount of one or more salicylic acid derivatives in the finished cosmetic or dermatological preparations is advantageously chosen from the range 0.1–15.0% by weight, preferably 0.5–8.0% by weight, based on the total weight of the preparations. If ethylhexyl salicylate is chosen, it is advantageous to choose its total amount from the range 0.1–5.0% by weight, preferably 0.5–2.5% by weight. If homomenthyl salicylate is chosen, it is advantageous to choose its total amount from the range 0.1–10.0% by weight, preferably 0.5–5.0% by weight.

The LPF of cosmetic or dermatological preparations comprising any of the UV filter substances described above, be it as individual substances or in any mixtures thereof, the total amount of such filter substances being, for example, from 0.1% by weight to 30% by weight, preferably 0.5 to 10% by weight, particularly from 1 to 6% by weight, based on the total weight of the preparations, is significantly increased according to the invention by the use of polysaccharides.

The examples below serve to illustrate the present invention without limiting it. Unless stated otherwise all quantities, proportions and percentages are by weight and based on the total amount or on the total weight of the preparations.

EXAMPLE 1

| O/W lotion | |
|---|---|
| | % by weight |
| Glyceryl stearate SE | 3.50 |
| Stearic acid | 1.80 |
| Cyclomethicone | 3.00 |
| Cetyl stearyl alcohol | 0.50 |
| Sodium hydroxide (45% strength) | 0.20 |
| Preservative | q.s. |
| Perfume | q.s. |
| Octyldodecanol | 7.00 |
| Dicaprylyl ether | 8.00 |
| Fucogel ® 1000 | 5.00 |
| Parsol ® 1789 | 2.00 |
| Eusolex ® 6300 | 4.00 |
| Uvinul ® T150 | 3.00 |
| Eusolex ® 232 | 3.00 |
| $TiO_2$ | 3.00 |
| ZnO | 3.00 |
| Carbomer | 0.20 |
| Water, demin. | ad 100.00 |

EXAMPLE 2

| Hydrodispersion gel | |
|---|---|
| | % by weight |
| Pemulen ® TR-1 | 0.50 |
| Ethanol | 3.50 |
| Cyclomethicone | 3.00 |
| Dimethicone | 1.50 |
| Sodium hydroxide (45% strength) | 0.55 |
| Preservative | q.s. |
| Perfume | q.s. |
| Octyldodecanol | 0.50 |
| Caprylic-capric acid triglyceride | 5.00 |
| Fucogel ® 1000 | 3.00 |
| Parsol ® 1789 | 2.00 |
| Eusolex ® 6300 | 4.00 |
| Uvinul ® T150 | 3.00 |
| Eusolex ® 232 | 3.00 |
| $TiO_2$ | 3.00 |
| ZnO | 3.00 |
| Carbomer | 0.02 |
| Water, demin. | ad 100.00 |

EXAMPLE 3

| O/W cream | |
|---|---|
| | % by weight |
| Glyceryl stearate SE | 3.50 |
| Stearic acid | 3.50 |
| Octyldodecanol | 5.00 |
| Cetyl stearyl alcohol | 3.00 |
| Sodium hydroxide (45% strength) | 0.35 |
| Preservative | q.s. |
| Perfume | q.s. |
| $C_{12}$–$C_{15}$-alkylbenzoate | 10.00 |
| Fucogel ® 1000 | 5.00 |
| Parsol ® 1789 | 2.00 |
| Eusolex ® 6300 | 4.00 |
| Uvinul ® T150 | 3.00 |
| Eusolex ® 232 | 3.00 |
| $TiO_2$ | 3.00 |

O/W cream

| | % by weight |
|---|---|
| ZnO | 3.00 |
| Carbomer | 0.20 |
| Water, demin. | ad 100.00 |

EXAMPLE 4

W/O lotion

| | % by weight |
|---|---|
| Dehymuls ® PGPH | 3.50 |
| Lameform ® TGI | 3.50 |
| Isohexadecane | 5.00 |
| Ceresine | 3.00 |
| Sodium hydroxide (45% strength) | 0.35 |
| Preservative | q.s. |
| Perfume | q.s. |
| $C_{12}$–$C_{15}$-alkyl benzoate | 10.00 |
| Fucogel ® 1000 | 4.50 |
| Vaseline | 2.00 |
| Parsol ® 1789 | 2.00 |
| Eusolex ® 6300 | 4.00 |
| Uvinul ® T150 | 3.00 |
| Eusolex ® 232 | 3.00 |
| $TiO_2$ | 3.00 |
| ZnO | 3.00 |
| Water, demin. | ad 100.00 |

EXAMPLE 5

O/W lotion

| | % by weight |
|---|---|
| Glyceryl stearate SE | 3.50 |
| Stearic acid | 1.80 |
| Cyclomethicone | 3.00 |
| Cetyl stearyl alcohol | 0.50 |
| Sodium hydroxide (45% strength) | 0.20 |
| Preservative | q.s. |
| Perfume | q.s. |
| Octyldodecanol | 7.00 |
| Dicaprylyl ether | 8.00 |
| Hyaluronic acid | 0.10 |
| Parsol ® 1789 | 2.00 |
| Eusolex ® 6300 | 4.00 |
| Uvinul ® T150 | 3.00 |
| Eusolex ® 232 | 3.00 |
| $TiO_2$ | 3.00 |
| ZnO | 3.00 |
| Carbomer | 0.20 |
| Water, demin. | ad 100.00 |

EXAMPLE 6

Hydrodispersion gel

| | % by weight |
|---|---|
| Pemulen TR-1 | 0.50 |
| Ethanol | 3.50 |
| Cyclomethicone | 3.00 |
| Dimethicone | 1.50 |
| Sodium hydroxide (45% strength) | 0.55 |
| Preservative | q.s. |
| Perfume | q.s. |
| Octyldodecanol | 0.5 |
| Caprylic/capric acid triglyceride | 5.0 |
| Hyaluronic acid | 0.3 |
| Parsol ® 1789 | 2.00 |
| Eusolex ® 6300 | 4.00 |
| Uvinul ® T150 | 3.00 |
| Eusolex ® 232 | 3.00 |
| $TiO_2$ | 3.00 |
| ZnO | 3.00 |
| Carbomer | 0.2 |
| Water, demin. | ad 100.0 |

EXAMPLE 7

O/W cream

| | % by weight |
|---|---|
| Glyceryl stearate SE | 3.50 |
| Stearic acid | 3.50 |
| Octyldodecanol | 5.00 |
| Cetyl stearyl alcohol | 3.00 |
| Sodium hydroxide (45% strength) | 0.35 |
| Preservative | q.s. |
| Perfume | q.s. |
| $C_{12}$–$C_{15}$-alkyl benzoate | 10.00 |
| Parsol ® 1789 | 2.00 |
| Eusolex ® 6300 | 4.00 |
| Uvinul ® T150 | 3.00 |
| Eusolex ® 232 | 3.00 |
| $TiO_2$ | 3.00 |
| ZnO | 3.00 |
| Hyaluronic acid | 0.20 |
| Carbomer | 0.20 |
| Water, demin. | ad 100.00 |

EXAMPLE 8

W/O lotion

| | % by weight |
|---|---|
| Dehymuls ® PGPH | 3.50 |
| Lameform ® TGI | 3.50 |
| Isohexadecane | 5.00 |
| Ceresine | 3.00 |
| Sodium hydroxide (45% strength) | 0.35 |
| Preservative | q.s. |
| Perfume | q.s. |
| $C_{12}$–$C_{15}$-alkyl benzoate | 10.00 |
| Parsol ® 1789 | 2.00 |
| Eusolex ® 6300 | 4.00 |
| Uvinul ® T150 | 3.00 |
| Eusolex ® 232 | 3.00 |
| $TiO_2$ | 3.00 |
| ZnO | 3.00 |
| Hyaluronic acid | 0.15 |
| Vaseline | 2.00 |
| Water, demin. | ad 100.00 |

What is claimed is:

1. A cosmetic or dermatological composition useful for protecting skin against the damaging effects of ultraviolet light, said composition comprising:
   a) one or more polysaccharides; and
   b) one or more triazine compounds having ultraviolet filter properties.

2. The cosmetic or dermatological composition according to claim 1, wherein the triazine compounds having ultraviolet filter properties are selected from the group consisting of:
   a) tris(2-ethylhexyl) 4,4',4"-(1,3,5-triazine-2,4,6-triyltriimino) trisbenzoate;
   b) 2,4-bis{[4-(2-ethylhexyloxy)-2-hydroxy]phenyl}-6-(4-methoxyphenyl)-1,3,5-triazine;
   c) 2,4-bis{[4-(3-sulphonato)-2-hydroxypropoxy)-2-hydroxy]phenyl}-6-(4-methoxyphenyl)-1,3,5-triazine, sodium salt;
   d) 2,4-bis{[4-(3-(2-propoxy)-2-hydroxypropoxy)-2-hydroxy]phenyl}-6-(4-methoxyphenyl)-1,3,5-triazine;
   e) 2,4-bis{[4-(2-ethylhexyloxy)-2-hydroxy]phenyl}-6-[4-(2-methoxyethylcarboxyl)phenylamino]-1,3,5-triazine;
   f) 2,4-bis{[4-(3-(2-propoxy)-2-hydroxypropoxy)-2-hydroxy]phenyl}-6-[4-(2-ethylcarboxyl)phenylamino]-1,3,5-triazine;
   g) 2,4-bis{[4-(2-ethylhexyloxy)-2-hydroxy]phenyl}-6-(1-methylpyrrol-2-yl)-1,3,5-triazine;
   h) 2,4bis{[4-tris(trimethylsiloxysilylpropoxy)-2-hydroxy]phenyl}-6-(4-methoxyphenyl)-1,3,5-triazine;
   i) 2,4-bis{[4-(2"-methylpropenyloxy)-2-hydroxy]phenyl}-6-(4-methoxyphenyl)-1,3,5-triazine; and
   j) 2,4-bis{[4-(1',1',1',3',5', 5',5'-heptamethylsiloxy-2"-methylpropoxy)-2-hydroxy]phenyl}-6-(4-methoxyphenyl)-1,3,5-triazine.

3. The cosmetic or dermatological composition according to claim 1, wherein the triazine compound having ultraviolet filter properties is 2,2'-methylenebis(6-(2H-benzotriazol-2-yl)-4-(1,1,3,3-tetramethylbutyl)phenol).

4. The cosmetic or dermatological composition according to claim 1, wherein the one or more polysaccharides are soluble in water, swellable in water and/or gellable with water.

5. The cosmetic or dermatological composition according to claim 1, wherein the one or more polysaccharides are selected from the group consisting of hyaluronic acid, chitosan and the product having Chemical Abstracts registry number 178463-23-5.

6. The cosmetic or dermatological composition according to claim 1, wherein the one or more polysaccharides comprise 0.1 to 20% by weight of the composition.

7. The cosmetic or dermatological composition according to claim 6, wherein the one or more polysaccharides comprise 0.5 to 10% by weight of the composition.

8. The cosmetic or dermatological composition according to claim 7, wherein the one or more polysaccharides comprise 1 to 5% by weight of the composition.

9. A method of protecting skin from the damaging effects of ultraviolet light comprising applying to said skin a protective effective amount of a cosmetic or dermatological composition according to any one of claims 1–8.

10. A method of increasing the ability of a cosmetic or dermatological composition to protect skin from the damaging effects of ultraviolet light, wherein said cosmetic or dermatological composition comprises one or more triazine compounds having ultraviolet filter properties, said method comprising applying said cosmetic or dermatological composition to said skin in the form of a cosmetic or dermatological composition according to any one of claims 1–8.

* * * * *